United States Patent [19]

DuBois

[11] Patent Number: 5,075,113

[45] Date of Patent: Dec. 24, 1991

[54] PRODUCTS COMPRISING AN EMULSION OF WATER AND OILY PARAFFINIC HYDROCARBONS WITH ADDED EXTRACTS OF LECITHIN AND PROCESSES FOR PRODUCTION

[76] Inventor: Jacques DuBois, 8, Boulevard Gambetta, 11100 Narbonne, France

[21] Appl. No.: 338,564

[22] Filed: Apr. 14, 1989

[30] Foreign Application Priority Data

Apr. 22, 1988 [FR] France .............................. 88 05565

[51] Int. Cl.$^5$ .............................................. A61K 37/22
[52] U.S. Cl. .................................... 424/450; 424/447; 424/449; 424/63; 424/70
[58] Field of Search .............. 424/450, 447, 449, 63, 424/78, 70

[56] References Cited

U.S. PATENT DOCUMENTS

| | | | |
|---|---|---|---|
| 4,205,088 | 5/1980 | Schoetensack et al. | 514/562 |
| 4,568,547 | 2/1986 | Herschler | 514/772 |
| 4,647,394 | 3/1987 | Kimura et al. | 252/117 |
| 4,701,469 | 10/1987 | Mendy | 514/547 |
| 4,791,140 | 12/1988 | Fukasawa et al. | 424/63 |
| 4,844,902 | 7/1989 | Grohe | 424/449 |

FOREIGN PATENT DOCUMENTS

| | | |
|---|---|---|
| 61-157340 | 7/1986 | Japan . |
| 62-175414 | 8/1987 | Japan . |
| 63-14706 | 1/1988 | Japan . |

OTHER PUBLICATIONS

Grant and Hackh's Chemical Dictionary, 5th Ed., pp. 422, 617.

*Primary Examiner*—Thurman K. Page
*Assistant Examiner*—Louis A. Piccone
*Attorney, Agent, or Firm*—Young & Thompson

[57] ABSTRACT

The invention provides new dietetic, laxative or cosmetic products which comprise an aqueous phase containing a proportion between 0.01 ane 10% by weight of water, an extract of lecithin enriched in phosphatidylcholine, which aqueous phase forms an emulsion with an oily phase comprised principally of paraffin hydrocarbons which are oily or solid at ambient temperature, for example vaseline and/or paraffin oil and of a liposoluble lecithin extract in proportions between 0.01 and 10% by weight of the paraffin hydrocarbons. The emulsion can moreover contain an inert mineral powder, such as kaolin, talc, calcium carbonate and/or monodiglycerides having a melting temperature above 50° C. An application is the preparation of spreadable dietetic or laxative products or cosmetic milks or creams.

1 Claim, No Drawings

PRODUCTS COMPRISING AN EMULSION OF WATER AND OILY PARAFFINIC HYDROCARBONS WITH ADDED EXTRACTS OF LECITHIN AND PROCESSES FOR PRODUCTION

The present invention has for its object new products, particularly dietetic, laxative or cosmetic products, comprising an emulsion of water and paraffinic hydrocarbons that are oily or solid at ambient temperature, with added extracts of lecithin and processes for making these products.

The technical field of the invention is that of the provision of dietetic, laxative or cosmetic products based on paraffinic hydrocarbons and extracts of lecithin.

In the field of food or diet, there are known numerous pasty products which can be spread on bread for example, butter, pates, cheese whip, fish spreads, etc.

The ability of these products to be spread on bread is due to their high level of lipids, which can vary from 82% for butter to about 40% for so-called light butter in which a portion of the butter is replaced by vegetable oils.

One of the present nutritional problems is the excessive richness of foodstuffs in lipids which gives rise to cardiovascular ailments and obesity.

A first object of the present invention is to provide pasty spreadable dietetic products in which all or a large part of the lipids assimilable by the organism are replaced by non-assimilable oily paraffinic hydrocarbons, which permits obtaining products which are spreadable despite the absence or small quantity of lipids and which have no or very low energy value.

There are already known dietetic or weight loss food products, in whose composition a portion or all of the fatty materials is replaced by mineral oils.

French Pat. No. 71/46,658 (Publication No. 2.165.312) M. KREMER, describes food products of low calorific power and more particularly pastries, pates, chocolate and pralines containing paraffin oil or vaseline and a natural emulsifying agent which can be lecithin.

French Pat. No. 652,995 (BECUNDIA HOLDING) discloses a process of making bread, in which is added to the dough an emulsion of paraffin oil, glycerine and water.

French Pat. No. 914,504 (N.S.B. Patents) discloses a process of making bread, pastry or similar products, in which is added to the flour a small quantity of paraffin wax and liquid hydrocarbons with or without the addition of small quantities of glycerine or lecithin.

French Pat. No. 933,429 (N.S.B. Patents) discloses a process in which is added to the dough an aqueous emulsion containing a mineral, vegetable or animal wax and an emulsifier which can be lecithin.

None of these prior patents disclose dietetic products in spreadable paste form comprised by an emulsion of an aqueous phase and an oily phase containing respectively an extract of hydrodispersible lecithin and an extract of liposoluble lecithin.

The three last patents cited relate exclusively to processes of making flour-based bread or pastries adapted to improve the shelf life of the bread.

French Pat. No. 71/46,658 relates to making food products such as baked pastries based on flour and eggs, chocolate, pralines or cooked meat and liver-based pates, which are food products very different from the pasty products according to the present invention, adapted to serve as substitutes for butter and margarine or in the preparation of spreadable pates.

It is known that paraffin oil promotes the intestinal transport and has a laxative effect.

However the oily consistency has a repulsive effect and many people are opposed to taking oily laxatives.

A second object of the present invention is to provide spreadable laxative pates easy to absorb.

There are known numerous cosmetic products for skin care such as day creams or night creams, toilet milks, solar creams, etc.

Most of these cosmetic products known to date contain in their formulation surface-active or synthetic tensio-active agents, which can be anionic agents (lauryl sulfate or lauryl ether sulfate) or cationic agents (quaternary ammonium) non-ionic or amphoteric.

However the synthetic surface-active agents have an aggressive action on living cells. When they are added, even in very low concentration, to in vitro cell cultures, there is observed a marked diminution in the multiplication of the cells and a morphological change of these latter.

Derma-cosmetic products are generally applied to the skin for relatively long periods, of the order of 8 to 10 hours and these applications are repeated.

The presence of synthetic cyto-toxic synthetic surface-active agents in their composition gives rise to skin reactions such as: reddening, irritation, itching.

In persons with sensitive skin or aged persons, or in babies, these reactions can lead to more serious skin troubles such as dermatitis, allergies, etc.

A third object of the present invention is to provide cosmetic products, particularly products for skin care, in which the tensio-active synthetic agents are replaced by natural emollients agents used in association with paraffin hydrocarbons, which have no aggressiveness toward living cells.

The objects of the invention are achieved by means of a family of new products which are emulsions of an aqueous phase in an oily phase.

The aqueous phase contains an extract of hydrodispersible lecithin, in a proportion between 0.1 and 5% by weight of the water. This lecithin extract is an extract enriched in phosphatidylcholine.

The oily phase is composed principally of oily paraffin hydrocarbons and a purified lipo-soluble lecithin extract in a proportion between 0.1 and 5% by weight of the hydrocarbons.

The proportion of the oily phase can vary between 5 and 90% of the total weight of the emulsion.

Preferably, the products according to the invention contain also an inert mineral powder, such as for example kaolin, talc or calcium carbonate in a proportion between 0.1 and 10% of the total weight which is suspended in the aqueous phase.

According to a preferred embodiment, the products according to the invention contain moreover monoglycerides having a melting temperature above 50° C. in a proportion between 0.05 and 10% of the total weight, which are melted and added to the oily phase.

The term paraffin hydrocarbons is used in scientific texts to designate all the saturated hydrocarbons of the formula $C_nH_{2n+2}$, which is to say the alcanes.

It is to be noted that this term is used in the present application to designate saturated hydrocarbons comprising in their molecule a higher number of hydrocarbons which at ambient temperature will be either in the oily state or in the solid or waxy state, as for example vaseline or paraffin oil or even paraffin per se, which is a solid which melts at a temperature between 43° C. and 65° C. In this last case, the paraffin is melted before being mixed with the lipo-soluble lecithin extract, then it is mixed with the aqueous phase to form an emulsion at a temperature at which it is clearly liquid.

The presence of a lipo-soluble lecithin extract in the aqueous phase permits obtaining emulsions of water and oil which are very stable, using as the emulsifying agent only extracts of lecithin which are non-toxic products of natural origin.

It will be recalled that the lecithins are phosphorylated lipids which are found in various vegetable or animal tissues.

Lecithin extracts are commercially available, particularly from egg yoke, milk, bone marrow, beans, soya, etc.

Lecithin plays an important role in the phenomena of cellular membrane permeability and in this way in the mechanisms of cellular metabolism.

There are commercially available lecithin extracts which are enriched in phosphatidylcholine and which are dispersible in water. These extracts are sold for example under the trade names "EPIKURON 145V" or "EMULPUR N." Also commercially available are purified lipo-soluble lecithin extracts which are sold for example under the trade name "EMULFLUID E".

The present invention permits obtaining several orders of products, particularly dietetic or laxative products in the form of spreadable paste and cosmetic products in the form of creams, gels or milks, applicable to the skin for skin care.

The dietetic products according to the invention have the appearance and consistency of butter or margarine, in which the oils assimilable by the organism are totally or in large part replaced by an emulsion of water and oily paraffin hydrocarbons, which are not assimilable, such that these products have very low calorific power.

If the hydrocarbon content is less than 45%, there are obtained dietetic spreadable pastes that have good olfactory-taste properties and good unctuosity, to which can be added various flavors such as banana, nut, chocolate, fruit for sugared pastes or even smoked salmon, anchovy, herbs, etc. for salty compositions.

When the of the paraffin hydrocarbon content of the emulsion is between 45 and 90%, there are obtained spreadable pastes having the appearance of margarine provided with laxative properties which permit providing gentle laxative formulations in a new presentation, easier to absorb by certain patients who are repelled by oily laxatives such as paraffin oil.

The edible products according to the invention have the advantage of containing no synthetic tensio-active substance, which might render the paraffin oil assimilable in the digestive tract. They take the form of stable spreadable pastes, which do not lose their water, which spread easily on bread, which melt at ambient temperature and which give in the mouth olfactory-taste properties which are very satisfying.

There will be described hereafter for illustrative purposes several non-limiting examples of the preparation of various spreadable products according to the invention.

Example No. 1: Preparation of a dietetic spreadable paste

In a 150 liter double bottomed stainless steel reactor, provided with a vacuum source and an agitator, there is first prepared an oily phase.

There is placed in the reactor:
- 35 kg of codex-quality paraffin oil with high viscosity;
- 5 kg of solid paraffin having a melting temperature higher than 45° C.;
- 0.3 kg of solid mono-glycerides having a melting temperature higher than 50° C.;
- 0.5 kg of commerically pure lecithin extract which is partially hydrolyzed and which is titrated in phosphatides and lipo-soluble lysophospholipids.

Hot water is circulated between the two walls of the double-walled reactor to bring the temperature to about 70° to 80° C., until the solid products are melted. Homogenization is carried out by agitation at low speed, of about 200 T/minute. Circulation of the hot water is cut off and the temperature is allowed to return to about 55° to 60° C. A coloring agent is added permitting the obtention of a paste of yellow color suggesting the color of butter. For example, there is added about 1 gram of 30% beta carotene. There is also added 100 grams of butter flavor.

Then there is prepared in a heating chamber an aqueous phase. There is poured into the chamber:
- 50.5 liters of purified water;
- 0.5 kg of hydrodispersible lecithin extract enriched in phosphatidylcholine, which is commercially available;
- 0.1 kg of a preservative, for example sodium benzoate;
- 2 kg of an inert mineral powder, for example purified kaolin powder.

The mixture is agitated to obtain a homogenous suspension and is heated to a temperature of about 55 to 60° C.

Once the aqueous phase is prepared, it is progressively pumped into the reactor containing the oily phase maintained under slow agitation at a temperature of about 55 to 60° C.

When all the liquid phase has been transferred to the reactor, a vacuum pump is actuated which lowers the pressure to about 6500 Pascal (65 mbars) and strong agitation is conducted at 500 turns/minute for about 10 minutes to form an emulsion of water and oil.

After this, the temperature is lowered to about 40° C., such that the paraffin and the monodiglycerides congeal.

The emulsion thus obtained is refined by passage through an homogenizer of the colloidal-mill type, then it is extruded through a sieve under a pressure of about 50 to 60 bars. The product obtained is paste which can be packaged in small tubs, then refrigerated. The paste can also be refrigerated at the outlet of the sieve and cut off in loafs or plates which are packaged like butter.

Example No. 2

An oily phase is prepared as above by placing in a reactor:
- 36.6 kg of codex-quality paraffin oil of low viscosity;
- 2.5 kg of a solid paraffin hydrocarbon having a melting temperature higher than 45° C.;
- 0.4 kg of solid mono-diglycerides having a melting temperature higher than 50° C.;

0.4 kg of partially hydrolyzed purified lecithin extract titrated with lysophospholipids which is soluble in hydrocarbons;

1 g of 30% beta carotene (colorant);

125 g of flavor, for example chocolate or nut flavor.

The preparation of the aqueous phase is the same as in Example 1 and the steps of the process of preparation of the emulsion are unchanged.

There is thus obtained a soft paste, more fluid than the previous one, which can be eaten as a dietetic desert.

The essential difference from Example No. 1 is that the quantity of solid paraffin is divided in half, which explains the softer consistency of the paste.

Example No. 3: Preparation of a dietetic "butter" of reduced fat

There is prepared an oily phase by placing in a reactor:

25 kg of codex-quality paraffin oil of high viscosity;

20 kg of butter or 15 kg of butter or vegetable oil;

0.5 kg of solid mono-glycerides having a melting temperature higher than 50° C.;

3.5 kg of solid paraffin having a melting temperature higher than 45° C.;

0.35 kg of purified lecithin extract, partially hydrolyzed, titrated with lysophospholipids;

100 grams of flavoring for example anchovy flavoring.

The aqueous phase is the same as in the two preceding examples. Salt is added.

There is thus obtained a dietetic product which contains only 16% of assimilable fatty material and which is in the form of a spreadable paste, which can be used for example on toast.

In the preceding examples, the aqueous phase contains 100 grams of a preservative agent which is sodium benzoate. This can be replaced by ascorbic acid, salicylic acid or sodium or potassium sorbate, associated with citric or ascorbic acid acting as flavoring and anti-oxidant additives.

In the preparation of the oily phase to obtain a light butter according to Example 3, 20 kg of butter can be replaced by 16 kg of deodorized fish oil, for example by flounder, cod fish, salmon oil, etc., which are of dietetic interest by reason of their content of unsaturated fatty acids such as gamma linoleic or linoleic acid.

The oil used is selected as a function of its deodorizing treatment and the presence of stabilizing agents, particularly anti-oxidants of the type of vitamin E.

Example No. 4: Preparation of a spreadable laxative paste

The oily phase is prepared by placing in a reactor:

65 kg of codex-quality paraffin oil of high viscosity;

6 kg of solid paraffin having a melting temperature higher than 45° C.;

0.5 kg of solid mono-diglycerides having a melting temperature above 50° C.;

0.6 kg of purified partially hydrolyzed lecithin extract titrated with lysophospholipids;

1 g of 30% beta carotene to obtain a color resembling that of butter;

150 g of an flavoring composition.

The steps of preparation of the aqueous phase and of the process of the preparation of the emulsion are the same as in Example No. 1.

There is finally obtained a paste which can be eaten with a spoon as a desert or spread on bread and which has laxative properties due to its high content of paraffin oil.

The preceding examples show that the processes according to the invention permit obtaining new dietetic or laxative compositions, comprised by an emulsion of an aqueous phase in an oily phase which is composed principally of oily or solid paraffin hydrocarbons, at ambient temperature, used alone or associated with animal or vegetable fats. The presence in these products of lipo-soluble lecithin extract and a hydro-dipersible extract of lecithin enriched in phosphatidylcholine permits obtaining very stable emulsions containing no synthetic surface-active agent. The compositions obtained are pasty products usable in dietetics as butter substitutes, as spreadable sugared or salted pastes or as creams edible with a spoon.

The processes according to the invention for the obtention of emulsions of water in an oily phase rich in paraffin hydrocarbons oily or solid at ambient temperature, permits also the preparation of cosmetic products applicable to the skin, in which the synthetic surface-active agents are replaced by extracts of lecithin.

The essential steps of the production processes remain the same as those of Examples Nos. 1 to 4 above. Only the compositions change.

Example No. 5: Preparation of a cosmetic cream

To obtain for example 100 kg of cream, there is prepared an oily phase by placing in a reactor:

15 kg of vaseline which is a mixture of paraffin hydrocarbons;

15 kg of paraffin oil;

0.5 kg of purified lipo-soluble lecithin extract titrated with lysophospholipids;

0.75 kg of solid mono-diglycerides having a melting temperature above 50° C.;

3 kg of vegetable oil, for example safflower oil.

There is also prepared an aqueous phase containing:

58 kg of purified water;

0.5 kg of hydrodispersible lecithin extract rich in phosphatidylcholine;

3 kg of inert mineral powder for example kaolin, 5 kg of sorbitol or glycerine;

0.075 kg of a preservative agent such as salicylic acid, ascorbic acid or benzoic acid;

several grams of perfume.

If desired, there can be added to the oily phase pigments in suspension in the case of solar creams or agents such as hydrating agents, acidifying agents, regenerative agents, protective agents, filtering agents, according to the use for which the cream is intended, this latter being adapted to be a night cream or day cream, a liquid body cream, a hand cream, a capillary cream, a complexion or sun cream, etc.

The resulting products having the consistency of a more or less fluid or pasty cream, easy to spread on the skin.

It is to be noted that the indicated quantities in Example 5 correspond only to a non-limiting example.

Generally speaking, the weight proportions of each product, to the total weight, may vary between the following limits in a skin care cream:

vaseline: between 0 and 45%, preferably about 12 to 25%;

paraffin oil: from 2.5 to 45%, preferably between 12 and 25%;

lipo-soluble lecithin extract: between 0.05 and 10%, preferably between 0.1 and 3%;

mono-diglycerides: between 0.05 and 10%, preferably between 0.1 and 3%:
vegetable oil: between 0 and 10%, preferably between 2 and 8%;
hydrodispersible lecithin extract: between 0.05 and 10%, preferably between 0.1 and 3%;
mineral powder: between 0.5 and 10%, preferably between 0.5 and 6%;
water: sufficient quantity to make up 100%;
sorbitol or glycerine: between 0 and 10%, preferably between 2.5 and 6%;
preservative agent: between 0.01 and 0.5%, preferably between 0.1 and 0.2%.

Example No. 6: Preparation of gel creams.

The following products are used, whose proportions are expressed in percentage of the total weight.

Oily phase vaseline: between 0 and 20%, preferably between 0 and 6% for example 0;
paraffin oil: between 0 and 20%, preferably between 2 and 15%, for example 11%;
vegetable oil: between 0 and 20%, preferably between 2 and 10%, for example 8%;
lipo-soluble lecithin extract: between 0.05 and preferably between 0.2 and 10%, for example 0.5%;
mono-diglycerides: between 0 and 6%, preferably between 0 and 0.6%, for example 0;

Aqueous phase sorbitol or glycerine: between 0 and 10%, preferably between 0 and 5%, for example 0.
inert mineral powder: between 0 and 10%, preferably between 0.5 and 6%, for example 0.5%;
hydrodispersible lecithin extract: between 0.05 and 10%, preferably between 0.1 and 3%, for example 1.5%;
gelling agent: between 0 and 1%, preferably between 0.2 and 1%, for example 0.7% (for example polycarboxypolyvinyl, trade name "CARBOPOL");
ethyl alcohol: between 1 and 60%, preferably between 1 and 10%, for example 10%.

In addition to the above essential constituents, there can be added several drops of perfume and several drops of triethanol amine to adjust the viscosity of the product.

The products according to Example 6 may be used for example as gels or creams for face care or body care, as sun creams, as extenders for principal ingredients.

They differ from creams according to Example 5 by the fact that they contain alcohol, a lesser quantity of the oily phase and a gelling agent which permits obtaining the consistency of a gel.

Example No. 7: Preparation of a make-up remover

The proportions are expressed in percentage by weight of the total.

Oily phase vaseline: between 0.5 and 10%, preferably between 0.5 and 2%, for example 0.5%;
paraffin oil: between 0.5 and 10%, preferably between 0.5 and 2%, for example 0.5%;
lipo-soluble lecithin extract: between 0.01 and preferably between 0.01 and 0.5%, for example 0.05%;
vegetable oil: between 0 and 10%, preferably between 0 and 5%, for example 0;
monodiglycerides: between 1 and 6%, preferably between 2.5 and 5%, for example 2.5%;
preservative agent: between 0 and 0.5%, preferably between 0.1 and 0.2%, for example 0.1% (salicylic acid or benzoic acid);

Aqueous phase sorbitol or glycerine: between 0 and 10%, preferably between 2.5 and 6%, for example 2.5%.
water: the quantity necessary to make up 100%;
lecithin extract: between 0.05 and 10%, preferably between 1 and 3%, for example 1.75%;
inert mineral powder: between 0.5 and 10%, preferably between 0.5 and 6%, for example 2.5% (for example kaolin);
gelling agent: between 0 and 0.5%, preferably between 0.1 and 0.25%, for example 0.15% (for example polycarboxypolyvinyl).

Several drops of perfume and several drops of triethanol amine can be added to adjust the viscosity.

Example No. 8: Preparation of an excipient base with low water content

The proportions are expressed in percentage of the total weight.

Oily phase vaseline: between 20 and 90%, preferably between and 70%, for example 68%;
paraffin oil: between 2 and 20%, preferably between 5 and 10%, for example 7%;
lipo-soluble lecithin extract: between 0.05 and 10%, preferably between 0.2 and 2%, for example 1%;
vegetable oil: between 0 and 10%, preferably between 0.5 and 2%, for example 1.7%;
mono-diglycerides: between 0.05 and 10%, preferably between 0.5 and 2%, for example 1.7%;
preservative agent: between 0 and 0.5%, preferably between 0.1 and 0.2%, for example 0.1%;

Aqueous phase sorbitol or glycerine: between 0 and 20%, preferably between 2 and 10%, for example 10%;
water: quantity necessary to make up 100%, for example 7%;
lecithin extract: between 0.05 and 10%, preferably between 0.1 and 3%, for example 0.9%;
inert mineral powder: between 0.5 and 10%, preferably between 0.5% and 6%, for example 2%.

Several drops of perfume and between 0 and 2% of vitamin E can be added.

This excipient base, which has a very low water content, can absorb its weight of water at the time of utilization.

It can serve as an excipient to which can be added a vitamin A acid, zinc sulfate, erythromycin.

Examples 5 to 8 disclose various cosmetic products adapted particularly for skin care, which are present in the form of an emulsion of an aqueous phase in an oily phase, comprised essentially of oily paraffin hydrocarbons, such as paraffin oil or vaseline and which contain also an extract of lecithin soluble in the oily phase and an extract of lecithin with a high phosphatidylcholine content which is dispersible in the aqueous phase.

The paraffin hydrocarbons perform the function of the bulk of the fat usually used in dermatological products to give them their unctuosity and to permit them to be spread on the skin in the form of a thin film.

The lecithin extracts replace the surface-active agents which have heretofore been used to stabilize the emulsions.

The presence of lecithin extracts in dermatological products increases their efficacy. Thus the lecithin applied to the skin has a very important surface function. It has the properties of hydrating, reconstituting and protecting. It increases the flexibility and elasticity of the skin and the cutaneous respiration. Moreover it protects the skin against the drying effects of surface-active agents.

Applied to the hair, the lecithin produces softening effects, it gives bulk, it improves dressability, it reduces electrostatic charges.

Lecithin has already been used as an additive in certain cosmetic products. However, it use has been limited to the role of an additive, by the fact that it is insoluble in water and, until now, it has been used only as an accessory component of the oily phase of certain cosmetic products or in association with synthetic surface-active agents.

The compositions according to the invention permit incorporating higher proportions of lipo-soluble or hydrodispersible extracts of lecithin, without the addition of any synthetic surface-active agent.

The cosmetic products according to the invention are prepared with the aid of natural emulsifiers and refined paraffin hydrocarbons, which have no aggressiveness or toxicity. These are true physiological formulations having common properties with the natural structures and the components of cellular membranes.

They have an exceptional biocompatibility which is manifested by the total absence of any skin irritation or allergy such as reddening, roughening, vasodilation, peeling, itching, etc.

This advantage is particularly important for products which must remain in contact with the skin or mucosa for long periods.

Tests undertaken with cosmetic compositions according to the invention have shown an exceptional tolerance, even in the case of application to abraded skin or to sores. In this latter case, the patients have appreciated the cooling sensation, the anesthetic effect and the acceleration of healing of the sores.

All the products described in Examples 1 to 8 have the common characteristic of being constituted by an emulsion of an aqueous phase and an oily phase with a proportion of oily phase between 5 and 90%, which oily phase is comprised totally or mostly of paraffin hydrocarbons which are oily or solid at ambient temperature, which are entirely liquid at the time of preparation of the emulsion and to which are added a lipo-soluble lecithin extract used in proportions comprised between 0.01 and 5% by weight of the hydrocarbons and which aqueous phase contains a hydrodispersible lecithin extract in proportions comprised between 0.01 and 5% by weight of the water, which lecithin extract is commerically available and is an extract having a high content of phosphatidylcholine and is dispersible in water.

In addition to the essential constituents recited above, the products according to the invention preferably contain an inert mineral powder, for example kaolin, talc or calcium carbonate which is suspended in the aqueous phase in proportions between 0.1 and 10% by weight of the total emulsion. This mineral powder has a stabilizing effect on the emulsion.

Moreover, the products according to the invention can also preferably contain monodiglycerides which have a melting point above 50° C. in proportions between 0.05 and 10% by total weight of the emulsion. These monodiglycerides have the effect of conferring on the products a pasty consistency at ambient temperature.

Preferably, the products according to the invention can contain small quantities of preservative agents such as benzoic acid, salicylic acid or ascorbic acid, or can also contain a small quantity of vegetable oil or fish oil or butter, perfumes, vitamins, coloring agents, etc.

What is claimed is:

1. A product consisting essentially of an emulsion of an aqueous phase consisting essentially of water and an extract of hydrodispersible leithin enriched in phosphatidylcholine in a proportion comprised between 0.01% and 5% of the weight of the water and an oily phase consisting essentially of paraffin hydrocarbons that are oily or solid at ambient temperature and lipo-soluble lecithin in a proportion comprised between 0.01% and 5% by weight of the paraffin hydrocarbons, the proportion of oily phase being between 5% and 90% by weight of the hole.

* * * * *